United States Patent [19]

Pomot et al.

[11] 4,080,438

[45] Mar. 21, 1978

[54] STARCH COATED ANTIPERSPIRANT DERIVATIVE OF ALUMINUM, PROCESS FOR ITS PREPARATION AND ANTIPERSPIRANT COMPOSITION CONTAINING THE SAME

[75] Inventors: Jean Pomot, Mouans Sartoux; Jean-Philippe Chalaye, Maisons-Alfort, both of France

[73] Assignee: L'Oreal, Paris, France

[21] Appl. No.: 613,020

[22] Filed: Sep. 12, 1975

Related U.S. Application Data

[63] Continuation-in-part of Ser. No. 438,944, Feb. 1, 1974, abandoned.

[30] Foreign Application Priority Data

Feb. 5, 1973    Luxembourg ............................ 66961

[51] Int. Cl.$^2$ ................................................ A61K 9/62
[52] U.S. Cl. ...................................... 424/35; 424/46; 424/47; 424/68
[58] Field of Search ...................... 424/47, 68, 46, 35

[56] References Cited

U.S. PATENT DOCUMENTS

| | | | |
|---|---|---|---|
| 3,300,387 | 1/1967 | Kole | 424/68 X |
| 3,637,657 | 1/1972 | Morii et al. | 424/180 X |
| 3,664,963 | 5/1972 | Pasin | 424/32 X |
| 3,691,271 | 9/1972 | Charle et al. | 424/47 X |

FOREIGN PATENT DOCUMENTS

| | | | |
|---|---|---|---|
| 368,458 | 3/1932 | United Kingdom | 424/68 |
| 903,407 | 8/1962 | United Kingdom | 424/68 |

OTHER PUBLICATIONS

Chem. Abs. 1970, vol. 72, p. 68456v.

*Primary Examiner*—Dale R. Ore
*Attorney, Agent, or Firm*—Cushman, Darby & Cushman

[57] ABSTRACT

An antiperspirant agent comprises microcrystals of an antiperspirant derivative of aluminum coated with degraded starch which gels in water at a temperature lower than 100° C so as to provide an atomizable gel having a starch composition between 5-30 weight percent thereof. The antiperspirant agent is present in the composition in amounts of about 2-10 weight percent thereof. The composition can be packaged as an aerosol.

21 Claims, No Drawings

STARCH COATED ANTIPERSPIRANT DERIVATIVE OF ALUMINUM, PROCESS FOR ITS PREPARATION AND ANTIPERSPIRANT COMPOSITION CONTAINING THE SAME

This application is a continuation-in-part of our application Ser. No. 438,944 filed Feb. 1, 1974, now abandoned.

The present invention relates to a new product usefully employed as an antiperspirant agent, to a process for producing this product, to an antiperspirant composition, packaged in the form of an aerosol which contains this product.

It is known that one of the methods to reduce, combat or eliminate body odor caused by decomposition of perspiration by microbial flora of skin involves the use of metallic astringent derivatives, such as aluminum derivatives which reduce the phenomenon of perspiration when applied to the skin.

Numerous aluminum astringent derivatives have been proposed or commercialized in the past. These aluminum derivatives are either salts or complexes which have been described, and the use of which as antiperspirants have been discussed, in numerous publications, among which are for example: Hibbot, Handbook of Cosmetic Science, Pergamon Press, 1963, pages 332-337; Alexander, Manufacturing Chemist and Aerosol News, December, 1969, pages 25-33; Blank et al, Proc. Scient. Sect. Toilet Goods Assn, (27), 24, 1957; Hopf. Jr. Med. Kosm. 1, 6, 1955; Brun, Dermatologica, 111, 316, 1955; Ichibashi, J. Orient. Med., 25, 105, 1936; Richardson et al, J. Soc. Cosmets, Chem, 2, 308 (1951); Sulzberger et al, Archs. Derm. Syph. 60, 404, 1949; Pillsbury, Dermatology, 36, 832, 1956; Papa, J. Soc. Cosmet. Chem., 17, 789, 1966; and Perry et al, Jr. Invest. Derm., 36, 7, 1961.

All these aluminum derivatives, which are well known to the skilled artisan, are usefully employed in the present invention and will hereafter be referred to as antiperspirant derivatives of aluminum.

For several years, the use of antiperspirant compositions packaged in the form of an aerosol has achieved wide acceptance. Such antiperspirant compositions are generally composed of an antiperspirant derivative of aluminum, such as, for example, micronized basic aluminum hydrochloride suspended in the aerosol propellant, and a perfume dissolved in the propellant, i.e., the continuous phase of the aerosol composition. Further, it has been known to include in these compositions such adjuvants as bactericides which function as deodorants, emollients and suspension agents to promote or enhance the homogeneity of the composition and thereby facilitate its passage through the distribution valve of the aerosol container.

However, conventional type antiperspirant compositions packaged in the form of an aerosol exhibit a certain number of significant disadvantages. One significant disadvantage of these known antiperspirants in aerosol form which contains both microcrystals of antiperspirant derivatives of aluminum in suspension in the propellant and a perfume in solution in the latter, is that frequently a chemical reaction takes place between these two components with the result that the perfume is often destroyed or changed, especially during storage of the aerosol compositions. Consequently certain perfumes which are particularly sensitive to this type of destructive action cannot be used even though their use is particularly desirable.

Moreover, after application to the skin, the microcrystals of the aluminum derivative when in direct contact with perspiration, produce, locally, very concentrated solutions which often cause irritation to users having sensitive skin.

Further, because of the irritant effect of antiperspirant derivatives of aluminum, certain disadvantages have been noted among those required to handle significant quantities of these materials, particularly during the production and packaging of antiperspirant compositions in the form of conventional aerosols.

It has now been discovered that the above disadvantages can be avoided by using as the antiperspirant agent in aerosol compositions, not a micronized antiperspirant derivative of aluminum in the free state, but rather particles of a hygroscopic antiperspirant derivative of aluminum having a coating of a polymer whose rate of solubilization in water at human body temperature is such that the liberation of the antiperspirant derivative of aluminum is more or less rapid on contact with perspiration.

Moreover, when the product according to the present invention is employed in aerosol compositions, the antiperspirant derivative of aluminum is isolated from other components of the aerosol which are in solution or in suspension in the propellant.

To obtain the desired effects, the particles of the coated microcrystals of the antiperspirant derivative of aluminum must possess certain chemical and physical properties. First, it is necessary that the coating material exhibit essentially no reactivity with the antiperspirant derivative of aluminum, which is generally not the case for a majority of polymers and especially for certain natural polymers such as polypeptides or gums such as gum arabic. It is also necessary that the polymer coating, at human body temperature, be soluble in water and perspiration so as to readily liberate the antiperspirant derivative of aluminum coated therewith. Moreover, when the coated antiperspirant derivative of aluminum is employed in an aerosol, it is necessary that the polymer coating material be essentially insoluble and not swell up in the propellant, the latter generally comprising a mixture of fluoronated hydrocarbons such as those known under the trademark "FREON". It is also necessary that the coated antiperspirant agent of this invention be impermeable to the propellant so that no other component in solution in the propellant, and particularly the perfume, can come into contact with the antiperspirant derivative of aluminum during storage in the aerosol container.

In addition to these requirements, it is preferable that the polymer coating material exhibits some cosmetic properties itself and especially that it be a softener for the skin.

Materials capable of satisfying these requirements are certain types of starch degraded by acid hydrolysis. Thus, the present invention has for an object a new product usefully employed as an antiperspirant agent comprising microcrystals of an antiperspirant derivative of aluminum coated by degraded starch which gels in water at a temperature lower than 100° C so as to provide an atomizable gel having a starch concentration between about 5-30 and preferably between 10-15 percent by weight thereof.

It is well known that there is often used in industry starches which are not in their raw or original state but rather starches which have been modified and principally starches modified by controlled acid hydrolysis. These starches are referred to in the present invention as "starch partially degraded by acid hydrolysis". These modifications by controlled acid hydrolysis are described in the literature, for example by Davidson and Sittig, "Water-Soluble Resins", Reinhold Book Corp. 2nd Ed. pages 30 and following.

The choice of a starch, partially degraded by acid hydrolysis, which is suitable for the preparation of the antiperspirant agent according to the present invention, can be effected by simple routine experimentation.

In effect, the phenomenon of gelification rests on the following observation. When an aqueous starch suspension is heated, no modification of the viscosity is observed until a certain temperature called the gelification temperature is attained. The gelification temperature is the temperature at which the starch granules begin to swell and rapidly hydrate, thus producing a significant increase in the viscosity.

In other words, to determine the starches which respond to the preceding definition, it suffices to put into suspension in water, a starch degraded by acid hydrolysis, and heat it. If gelification occurs before reaching 100° C, the starch responds to the preceding definition. If gelification does not occur, the starch is not useful for the preparation of an antiperspirant agent of the present invention.

The phenomenon of gelification, such as has been explained above, has been studied and reported in detail in such works as that by Davidson and Sittig, "Water-soluble Resins", Reinhold Book Corp. 2nd Ed. pages 19–21.

Further, it is known that there exists waxy cornstarch and ordinary cornstarch. The characteristics of these two types of cornstarch are described in numerous publications including, for instance, Kirk-Othmer, Encyclopedia of Chemical Technology, 2nd Ed. Vol. 18.

Representative starches having these properties are those degraded by acid hydrolysis and principally waxy cornstarch degraded by hydrolysis to a Stormer viscosity of 85, such as that commercially available under the name "AMIOCA" by National Starch Company or ordinary cornstarch degraded by hydrolysis to a Stormer viscosity of 65, such as that commercially available under the mark "FLUITEX" by National Starch Company, or, again, starches of different origins degraded by hydrolysis to dextrin.

Representative antiperspirant derivatives of aluminum usefully employed in the present invention include aluminum halides such as basic aluminum hydrochloride and basic aluminum hydrobromide, complexes of aluminum hydroxy chloride with propylene glycol (see U.S. Pat. No. 3,359,169) such as that sold under the commercial name "Rehydrol" (Martin et al, Drug. Cosmet. Ind. 99 (5), 54, 1966), aluminum phenosulfonate, chlorhydroxy aluminum allantoinate or dihydroxy aluminum allantoinate (S. B. Mecca, Proceedings of the Scientific Section of the Toilet Goods Association, No. 31, May 1969), complexes of chlorhydroxy aluminum with propylene glycol such as that known under the commercial name As-Alcloxa, chlorhydroxy aluminum lactate such as that known under the commercial name of "Chloracel" (Kalish, Drug & Cosmet. Ind., September 1956), aluminum sulfamate, derivatives of 2-chloro dioxalumane such as those described in U.S. Pat. No. 3,444,226, derivatives of dioxalumane or dioxalumin substituted by electro-attractive groups such as those described in Luxembourg Pat. No. 64,463, aluminum derivatives of pyridine such as those described in Luxembourg Pat. No. 65,350 corresponding to U.S. application Ser. No. 294,072, filed Oct. 2, 1972, now U.S. Pat. No. 3,953,450 or mixtures thereof.

Representative derivatives of 2-chloro dioxalumane disclosed in U.S. Pat. No. 3,444,226 include for example 2-chloro-4-ethyl-6-methyl-1,3,2-dioxaluminane, 2-chloro-1,3,2-dioxaluminane, 2-chloro-4-methyl-1,3,2-dioxaluminane, 2-chloro-5-hydroxy-1,3,2-dioxaluminane and 2-chloro-4-propyl-5-ethyl-1,3,2-dioxaluminane.

The derivatives of dioxaluminane or dioxaluminin substituted by electro-attractive groups described in Luxembourg Pat. No. 64,463 have the following formulas:

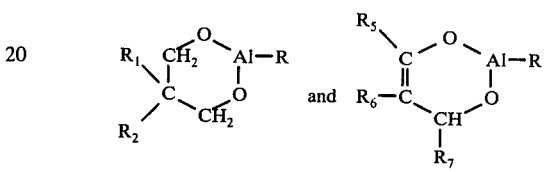

wherein $R_1$ is —CO—CH$_3$, —CO—C$_2$H$_5$ or —CO—phenyl and in which case $R_2$ is hydrogen or methyl,
or $R_1$ is —CN or —COO—alkyl having 1–4 carbon atoms in which case $R_2$ is hydrogen, methyl, —CN or —COO—alkyl having 1–4 carbon atoms,
or $R_1$ is —NO$_2$, in which case $R_2$ is halogen such as chlorine or bromine, hydrogen, alkyl having 1–4 carbon atoms or phenyl,
$R_7$ is hydrogen or alkyl having 1–6 carbon atoms,
$R_6$ is —CO—CH$_3$ or —CO—phenyl, in which case $R_5$ is methyl or phenyl, or
$R_6$ is —CN or —COO—alkyl having 1–4 carbon atoms, in which case $R_5$ is methyl, phenyl or —O—alkyl having 1–4 carbon atoms.

Representative of these compounds are:
2-chloro-5,5-bis-(ethoxy carbonyl)-1,3,2-dioxalumane,
2-chloro-5-cyano-5-ethoxy carbonyl-1,3,2-dioxalumane,
2-chloro-5-bromo-5-nitro-1,3,2-dioxalumane,
2-chloro-5-ethoxy carbonyl-4-ethoxy-1,3,2-dioxalumin,
2-chloro-5-ethoxy carbonyl-4-methyl-1,3,2-dioxalumin,
2-chloro-5-acetyl-4-methyl-1,3,2-dioxalumin and
2-methanesulfonyloxy-5,5-bis(ethoxy carbonyl)-1,3,2-dioxalumane.

The aluminum derivatives of pyridine described in Luxembourg Pat. No. 653,350 have the formula:

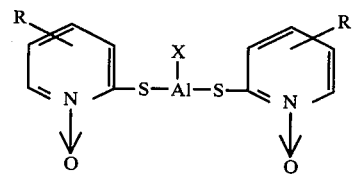

wherein X is chlorine, bromine or $R_1SO_3$— wherein $R_1$ is alkyl having 1–4 carbon atoms, phenyl, chlorophenyl, p-hydroxyphenyl or 2-oxo-10-bornanyl, and R is hydrogen, chlorine, methyl or methoxy.

Representative pyridine derivatives include:
bis-(N-oxypyridyl-2 thio) aluminum chloride,
bis-(N-oxypyridyl-2 thio) aluminum bromide,
bis-(N-oxypyridyl-2 thio) aluminum camphosulfonate,
bis-(N-oxypyridyl-2 thio) aluminum p-toluenesulfonate, bis-(N-oxypyridyl-2 thio) aluminum p-hydroxybenzene sulfonate,
bis-(N-oxypyridyl-2 thio) aluminum methanesulfonate,
bis-(4-chloro-N-oxypyridyl-2 thio) aluminum chloride,
bis-(6-chloro-N-oxypyridyl-2 thio) aluminum chloride,
bis-(4-methoxy-N-oxypyridyl-2 thio) aluminum p-chlorobenzenesulfonate,
bis-(6-methoxy-N-oxypyridyl-2 thio) aluminum bromide,
bis-(chloro-N-oxypyridyl-2 thio) aluminum camphosulfonate, and
bis-(6-methyl-N-oxypyridyl-2 thio) aluminum chloride.

In order to facilitate its use in aerosols, the product of the present invention can advantageously be produced in the form of a powder consisting of finely divided particles having a particle diameter between 10-50 microns and preferably between 20-30 microns. This dimension is particularly favorable to the passage through the distribution valve of the aerosol container and lends itself to good adherence of the particles to the skin.

The present invention also relates to a process for obtaining the product defined above, the said process comprising introducing into a current of air at an elevated temperature, generated for example in an atomizer drier, an aqueous gel of the starch defined above containing in solution an antiperspirant derivative of aluminum. The aqueous gel of degraded starch can be obtained by producing a suspension of starch in cold water; heating this suspension, with the agitation, to a temperature of 80°-90° C and preferably about 85° C so as to impart fluidity to the gel; and then adding thereto the antiperspirant derivative of aluminum, either in the form of crystals, or in the form of an aqueous solution of conventional concentration, for example a 30 to 55% solution of basic aluminum hydrochloride. The resulting gel containing the antiperspirant derivative of aluminum is maintained at a temperature between 80°-90° C during its introduction into the atomizer drier. The temperature of the air at the inlet of the atomizer drier, which can be of conventional design, can be maintained between 200°-230° C, and the exit temperature can be maintained at, for example 110°-120° C.

The concentration of antiperspirant derivative of aluminum employed in the starch gel can be determined by the weight ratio of the antiperspirant derivative of aluminum to starch (dry basis) that is desired in the final product. Conveniently, this weight ratio is advantageously between 1:10 and 1:1.

The present invention also relates to an antiperspirant composition comprising in an appropriate cosmetic vehicle or carrier, the product defined above. The cosmetic vehicle or carrier is one suitable for topical application to human skin.

The expression "cosmetic vehicle" as employed in the present invention includes all the components of the composition other than the active component, which components thus serve as the vehicle for this active product. The term "cosmetic" as employed in the present invention indicates simply that this vehicle must be able to be applied without any deleterious effect on the skin of the user. The components constituting the vehicle of the deodorant or antiperspirant compositions of the present invention are described in well known works on cosmetology and are designated generally by the expression "cosmetic vehicle". See for example Handbook of Cosmetic Science, cited above, page 332, 9th line from the bottom.

The antiperspirant compositions according to the present invention are principally compositions packaged in the form of aerosols which include, in addition to the product coated in accordance with the invention, an aerosol propellant agent. This propellant agent functions to provide within the aerosol container a pressure sufficient to permit progressive release of the contents of the container through the distribution valve of said container.

It is known that propellant agents generally comprise a liquid or liquefied fluorinated hydrocarbon or a mixture thereof such as those sold under the name "FREON". These aerosol propellant agents are well known and are referred to in the present invention as a fluorohydrocarbon aerosol propellant agent. These propellant agents are principally fluoronated derivatives of methane or ethane and the propellants most often utilized are dichlorodifluoromethane (Freon 12), trichlorofluoromethane (Freon 11), and dichlorotetrafluoroethane (Freon 114). In practice, there is generally used either a mixture of Freon 11 and 12 or a mixture of Freon 12 and 114.

It is also well known that there can also be used as a propellant agent, $CO_2$ or nitrous oxide under pressure, in combination with a fluorohydrocarbon propellant agent in which the $CO_2$ or nitrous oxide is partially dissolved. Thus there can be employed, for example, as the aerosol propellant agent, Freon 11 and $CO_2$, or Freon 11 and nitrous oxide; see, for instance, Belgium Pat. No. 763,982.

Publications relating to the production of cosmetic compositions, packaged in the form of aerosols, and in particular those employing fluorohydrocarbon propellant agents, include the work of Hibbot, Handbook of Cosmetic Science, Pergamon Press (1963), Chapter XXIV, as well as the references mentioned in this chapter.

The cosmetic compositions in the form of aerosols according to the present invention can contain, for example, other active components and propellant agents, a perfume, a suspension agent to assist the homogeneity of the mixture such as colloidal silica, and an emollient such as isopropyl palmitate or myristate, or a mixture of these various cosmetic adjuvants of aerosols.

The cosmetic vehicle, when the composition is in the form of an aerosol, is then principally constituted by the aerosol propellant agent, and optionally the perfume, emollient and/or suspension agent.

Additionally, the antiperspirant composition in the form of an aerosol according to the present invention can contain a conventional bactericidal deodorant agent such as, for example, Irgason D.P. 300 (2,4,4'-trichloro-2'-hydroxy diphenyl ether).

Bactericidal deodorant agents used in the deodorant compositions are described in the literature such as the Handbook of Cosmetic Science, pages 332-334. One of the most well known deodorant agents is hexachlorophene.

The perfume useful in the antiperspirant compositions of the present invention are well known and are disclosed, for instance, in the work of Heizka, International Encyclopedia of Aerosol Packaging, Pergamon, Oxford (1965).

Thus, in the antiperspirant compositions of the present invention, there can be employed for example perfumes sold under the following names: Colmen 13182g and Leralia 18770 (Firmenich), Vervia C7 and 20247

(Creat Aromatiques), VIC8 and F.N. 3083 (IFF) and E1048 (Aromescence).

The compositions of the invention can also be presented in the form of powders called "talcs".

The preparation of these "talcs", and the nature of the cosmetic vehicles used in such compositions, are described for example in the Handbook of Cosmetic Science, cited above, particularly at pages 339-344.

In addition to the active component, these powders can contain a cosmetic vehicle constituted by talc, which is the most abundant component (60-90 weight percent, generally) perfumes and generally at least one of the following components in the form of a suitable ground powder: titanium oxide, zinc oxide, kaolin, colloidal silica, chalk, calcium phosphate, magnesium carbonate, zinc stearate and magnesium stearate.

Advantageously, such compositions can be packaged in the form of an aerosol and can contain in addition to the coated product of the present invention, a conventional aerosol propellant such as a mixture of fluoronated hydrocarbons. The antiperspirant composition of this invention can also contain, for example, a perfume; a suspension agent, such as colloidal silica; an emollient such as isopropyl palmitate or myristate; and a conventional deodorizing bactericide; or a mixture of two or more of these cosmetic adjuvants.

The coated antiperspirant derivative of this invention can be present in the antiperspirant composition of this invention in amounts of about 2-10, and preferably 3-5 percent by weight of said composition.

The following examples are given to illustrate the present invention.

EXAMPLE A 100 g of ordinary cornstarch, previously hydrolyzed to a Stormer viscosity of 65, and available under the mark "FLUITEX", are suspended in 900 centiliters of distilled water. The suspension is heated with vigorous agitation to a temperature of 85° C, at which temperature there is observed gelling of the starch and an increase in the viscosity of the mixture. 25 g of crystallized basic aluminum hydrochloride are then added and dissolved instantly.

The resulting gel is maintained at 85° C and charged to the feed end of an atomizer drier by means of a peristaltic pump. The temperature of the air at the inlet to the atomizer drier is maintained at 215° C during the time of atomization, the exit temperature being between 110°-115° C.

At the end of the operation there are recovered from the cyclone of the atomizer drier 120 g of fine powder comprising particles having a diameter between 15-40 microns and having the following composition:
Basic aluminum hydrochloride — 1 pbw
Starch — 4 pbw

EXAMPLE B 100 g of waxy maize starch hydrolyzed to a Stormer viscosity of 85 and available under the mark "AMIOCA" are suspended in 850 centiliters of distilled water. The suspension is vigorously agitated and progressively brought to a temperature of 85° C. At this stage, a partial dissolution of the starch and an increase in viscosity of the mixture occur.

With continued agitation, 50 g of basic aluminum hydrochloride in solution in 100 ml of water are added thereto.

The resulting gel, maintained with agitation at a temperature of 85° C, is then dried with atomization under the same conditions as those described in Example A. From the cyclone of the atomizer drier, 142 g of fine powder are recovered. The individual particles of the powder have a diameter between 10-40 microns and have the following composition:
Basic aluminum hydrochloride — 1 pbw
Starch — 1 pbw

EXAMPLE C

In accordance with the procedures employed in Example A, 100 g of Chloracel are coated with 100 g of Fluitex starch. The product obtained has the following composition:
Chloracel — 1 pbw
Fluitex starch — 1 pbw

EXAMPLE D

In accordance with the procedures employed in Example A, 100 g of Rehydrol are coated with 100 g of Fluitex starch. The product obtained has the following composition:
Rehydrol — 1 pbw
Fluitex starch — 1 pbw

EXAMPLE E

In a container cooled by a stream of water, there are dissolved, by introducing the same in small fractions, and by agitating the mixture, 1180 g of 2-chloro-5-ethoxy carbonyl-4-methyl, 1,3,2-dioxalumin in 3000 g of distilled water, without exceeding 30° C.

Separately, 1800 g of Fluitex starch are dispersed in 6000 g of distilled water, with good agitation and the resulting dispersion is heated progressively up to 85° C, the temperature at which the starch gels. The gel is cooled to 30° C and then mixed with the above dioxalumin solution. The resulting mixture is passed through an atomizer drier, the temperature of the air at the entrance of which is maintained at 200° C, while the temperature of the air at the exit thereof is 110° C.

At the end of the operation, there are recovered 2290 g of fine powder composed of particles having a diameter of 15-40 $\mu$ and having the following composition:
2-chloro-5-ethoxy carbonyl-4-methyl-1,3,2-dioxalumin — 1 pbw
Starch — 1 pbw

EXAMPLE F 1190 g of Fluitex starch are suspended in 12000 g of distilled water. The suspension is heated with vigorous agitation to a temperature of 85° C, the gelification temperature of the starch, at which point 1190 g of 2-chloro-5,5-bis-(ethoxy carbonyl)-1,3,2-dioxalumane are then added thereto.

The resulting gel is maintained at 85° C under agitation and put through an atomizer dryer. The temperature of the air at the inlet of the atomizer dryer is maintained at 200° C for the entire operation, the temperature of the air at the exit thereof being 110° C.

At the end of the operation, there are recovered 2273 g of fine powder composed of particles having a diameter of 15-40 $\mu$ and having the following composition:
2-chloro-5,5-bis-(ethoxycarbonyl)-1,3,2-dioxalumane — 1 pbw
Starch — 1 pbw

EXAMPLE G

In accordance with the procedures outlined in Example A, 100 g of micronized basic aluminum bromide are coated with 200 g of "Amioca" starch.

The product obtained has the following composition:
Basic aluminum bromide — 1 pbw
"Amioca" starch — 2 pbw

EXAMPLE H

In accordance with the procedures outlined in Example E, 40 g of basic aluminum bromide are dissolved in 60 g of water, thus providing solution (1).

Separately, 80 g of Fluitex starch are gelatinized at 85° C in 660 g of water, thus providing component (2). To component (2), cooled to 30° C, solution (1) is added at this same temperature.

The resulting mixture is then passed through an atomizer dryer. The temperature of the air at the inlet of the dryer is maintained at 200° C, while the temperature of the air at the exit thereof is 110° C.

At the end of the operation, there are recovered 117 g of fine powder composed of particles having a diameter of 15 to 40 $\mu$ and having the following composition:
Basic aluminum bromide — 1 pbw
Fluitex starch — 2 pbw

EXAMPLE I 50 g of Fluitex starch are gelatinized in 500 g of water which is then cooled to 30° C.

There are slowly added to the gel 25 g of 2-chloro-5-cyano-5-ethoxycarbonyl-1,3,2-dioxalumane which is very strongly agitated using a turbine agitator turning at 20,000 rpm.

The fine suspension obtained is passed through an atomizer dryer operating under the following conditions:
Temperature of the air at the inlet - 200° C;
Temperature of the air at the exit - 110° C.

There are recovered 71 g of powder having the following composition:
2-chloro-5-cyano-5-ethoxy carbonyl-1,3,2-dioxalumane — 1 pbw
Starch — 2 pbw In a similar fashion the following antiperspirant agents in accordance with the present invention having the following compositions are prepared. The numbers in parentheses indicate the parts by weight of the respective components:

EXAMPLE J 2-chloro-4-ethyl-6-methyl-1,3,2-dioxalumane/waxy cornstarch partially degraded by acid hydrolysis to a Stormer viscosity of 85 - (0.1:1).

EXAMPLE K 2-chloro-4-propyl-5-ethyl-1,3,2-dioxalumane/starch partially degraded by acid hydrolysis up to the production of a dextrin - (1:1).

EXAMPLE L 2-chloro-5-ethoxy carbonyl-4-ethoxy-1,3,2-dioxalumin/Amioca starch - (0.8:1).

EXAMPLE M 2-chloro-5-acetyl-4-methyl-1,3,2-dioxalumin/ordinary cornstarch partially degraded by acid hydrolysis to a Stormer viscosity of 65 - (0.4:1).

EXAMPLE N

Bis-(N-oxypyridyl-2 thio) aluminum bromide/Fluitex starch - (0.3:1).

EXAMPLE O

Bis-(6-methoxy-N-oxypyridyl-2 thio) aluminum bromide/Fluitex starch - (0.6:1).

EXAMPLE P

Bis-(4-chloro-N-oxypyridyl-2 thio) aluminum chloride/waxy cornstarch partially degraded by acid hydrolysis to a Stormer viscosity of 85 - (0.5:1).

The following examples illustrate antiperspirant compositions prepared in accordance with the present invention.

EXAMPLE 1

An antiperspirant composition packaged under pressure as an aerosol is prepared by admixing the following components:

| | |
|---|---|
| Basic aluminum hydrochloride coated as in Example A, powder | 4.00 g |
| Colloidal silica (Aerosil 300 - Degussa) | 0.30 g |
| Perfume | 0.50 g |
| Isopropyl myristate | 5.20 g |
| Trichlorofluoromethane | 45.00 g |
| Dichlorodifluoromethane | 45.00 g |
| | 100.00 g |

EXAMPLE 2

An antiperspirant composition packaged under pressure as an aerosol is prepared by admixing the following components:

| | |
|---|---|
| Basic aluminum hydrochloride coated as in Example B | 4.00 g |
| Colloidal silica (Aerosil R 972 - Degussa) | 0.30 g |
| Irgosan DP 300 | 0.10 g |
| Perfume | 0.60 g |
| Isopropyl palmitate | 5.00 g |
| Trichlorofluoromethane | 45.00 g |
| Dichlorodifluoromethane | 45.00 g |
| | 100.00 g |

EXAMPLE 3

An antiperspirant packaged under pressure in an aerosol container is prepared by admixing the following components:

| | |
|---|---|
| Product obtained in Example E | 5.25 g |
| Isopropyl palmitate | 3.00 g |
| Perfume - Colmen 13182g (Firmenich) | 0.40 g |
| Trichlorofluoromethane | 54.00 g |
| Dichlorodifluoromethane | 37.35 g |
| | 100.00 g |

EXAMPLE 4

An antiperspirant composition packaged under pressure in an aerosol container is prepared by admixing the following components:

| | |
|---|---|
| Product obtained in Example F | 5.25 g |

-continued

| Isopropyl myristate | 3.50 g |
|---|---|
| Perfume - Vervia 7C7 (Creat Aromatiques) | 0.50 g |
| Trichlorofluoromethane | 45.00 g |
| Dichlorodifluoromethane | 45.75 g |
| | 100.00 g |

EXAMPLE 5

An antiperspirant composition packaged in an aerosol container under pressure has the following composition:

| Product obtained in accordance with Example H | 5.00 g |
|---|---|
| Colloidal silica | 0.30 g |
| Isopropyl palmitate | 4.20 g |
| Perfume - E 1048 (Aromescence) | 0.50 g |
| Trichlorofluoromethane | 90.00 g |
| | 100.00 g |

The above mixture is placed in a 100 cm³ aerosol container and then saturated with nitrous oxide under pressure so as to establish a pressure therein of 5 kg/cm².

Similar antiperspirant compositions are produced by replacing the compound of Example H by that of Example M or P.

EXAMPLE 6

An aerosol antiperspirant composition having the following composition is prepared:

| Product of Example G | 4.5 g |
|---|---|
| Colloidal silica | 0.4 g |
| Isopropyl myristate | 3.6 g |
| Perfume - VIC 8 (IFF) | 0.5 g |
| Trichlorofluoromethane | 91.00 g |
| | 100.00 g |

The above mixture is placed in a 100 cm³ aerosol container and is then saturated with $CO_2$ under pressure to establish a pressure of 4.5 kg/cm² therein.

A similar antiperspirant composition is prepared by replacing the product of Example G with the product of Example I.

EXAMPLE 7

An antiperspirant composition packaged in the form of an aerosol and having the following composition is prepared:

| Product of Example B | 6.00 g |
|---|---|
| Isopropyl palmitate | 7.00 g |
| Perfume - F.N. 3083 (IFF) | 0.70 g |
| colloidal silica | 0.30 g |
| Dichlorodifluoromethane | 68.00 g |
| Dichlorotetrafluoroethane | 68.00 g |

A similar antiperspirant composition is prepared by replacing the product of Example B by the product of Example O.

EXAMPLE 8

An antiperspirant composition packaged under pressure in an aerosol container and having the following composition is prepared:

| Product of Example J | 10.00 g |
|---|---|
| Isopropyl myristate | 4.00 g |
| Colloidal silica | 0.30 g |
| Perfume - E1048 (Aromescence) | 0.50 g |
| Trichlorofluoromethane | 40.00 g |
| Dichlorodifluoromethane | 45.20 g |

EXAMPLE 9

An antiperspirant composition packaged under pressure in an aerosol container and having the following composition is prepared:

| Product of Example N | 5.30 g |
|---|---|
| Isopropyl palmitate | 3.00 g |
| Perfume - Vervia C7 (Creat Aromatiques) | 0.40 g |
| Colloidal silica | 0.30 g |
| Trichlorofluoromethane | 54.00 g |
| Dichlorodifluoromethane | 37.00 g |

EXAMPLE 10

An antiperspirant composition packaged under pressure in an aerosol container and having the following composition is prepared:

| Product of Example K | 2.00 g |
|---|---|
| Colloidal silica | 0.20 g |
| Perfume - E 1048 (Aromescence) | 0.30 g |
| Isopropyl myristate | 3.00 g |
| Trichlorofluoromethane | 49.50 g |
| Dichlorodifluoromethane | 45.00 g |

Similar antiperspirant compositions are prepared by replacing the product of Example K by the product of Example C or Example D.

EXAMPLE 11

An antiperspirant composition packaged under pressure in an aerosol container and having the following composition is prepared:

| Compound of Example L | 3.00 g |
|---|---|
| Isopropyl palmitate | 3.00 g |
| Perfume - Colmen 13182 g (Firmenich) | 0.40 g |
| Trichlorofluoromethane | 53.60 g |
| Dichlorodifluoromethane | 40.00 g |

EXAMPLE 12

An antiperspirant talc having the following composition is prepared:

| Talc | 80.00 g |
|---|---|
| Zinc oxide | 3.00 g |
| Magnesium stearate | 5.00 g |
| Colloidal silica | 1.00 g |
| Product of Example A | 10.00 g |
| Perfume | 1.00 g |

Similar antiperspirant talcs are prepared by replacing the product of Example A by that of Example J or Example N.

EXAMPLE 13

An antiperspirant talc is prepared by mixing and grinding to a powder the following components:

| | |
|---|---|
| Talc | 75.00 g |
| Kaolin | 10.00 g |
| Zinc stearate | 5.00 g |
| Colloidal silica | 1.00 g |
| Perfume | 1.00 g |
| Product of Example B | 8.00 g |

Similar antiperspirant talcs are prepared by replacing the product of Example B by the product of Examples G, H, I or P.

EXAMPLE 14

An antiperspirant talc is prepared having the following composition:

| | |
|---|---|
| Talc | 85.00 g |
| Titanium oxide | 3.00 g |
| Magnesium carbonate | 1.00 g |
| Calcium carbonate (chalk) | 5.00 g |
| Perfume | 1.00 g |
| Product of Example C | 5.00 g |

Similar antiperspirant talcs are prepared by replacing the product of Example C by the product of Examples D, E, F, K or L.

These compositions exhibit prolonged storage characteristics without essentially any chemical action between the perfume and the antiperspirant agent. Further, they cause no irritation to the skin when applied thereto.

What is claimed is:

1. An antiperspirant agent in the form of a dry powder comprising microcrystals of an antiperspirant derivative of aluminum coated with a starch degraded by acid hydrolysis which gels in water at a temperature lower than 100° C so as to provide an atomizable gel having a starch concentration between 5-30 weight percent thereof, wherein the weight ratio of antiperspirant derivative of aluminum to starch (dry basis) is between 1:10 and 1:1.

2. The antiperspirant agent of claim 1 wherein the starch is one which provides an atomizable gel at a concentration between 10-15 weight percent thereof.

3. The antiperspirant agent of claim 1 wherein said starch is ordinary cornstarch degraded by hydrolysis to a Stormer viscosity of 65.

4. The antiperspirant agent of claim 1 wherein said starch is waxy cornstarch degraded by hydrolysis to a Stormer viscosity of 85.

5. The antiperspirant agent of claim 1 wherein said starch is a starch degraded by hydrolysis to dextrin.

6. The antiperspirant agent of claim 1 wherein said antiperspirant derivative of aluminum is basic aluminum hydrochloride.

7. The antiperspirant agent of claim 1 wherein the diameter of the particles of said powder ranges between 10-50 microns.

8. An antiperspirant composition comprising in a talc or aerosol the antiperspirant agent of claim 1 in an amount of 2-10 percent by weight of said composition.

9. The antiperspirant composition of claim 8 packaged under pressure in an aerosol container together with an aerosol propellant.

10. The antiperspirant composition of claim 9 wherein said antiperspirant agent is present in amounts of 3-5 percent by weight of said composition.

11. The antiperspirant composition of claim 9 wherein said antiperspirant agent contains, as an antiperspirant derivative of aluminum, basic aluminum hydrochloride.

12. The antiperspirant composition of claim 9 wherein said antiperspirant agent is an antiperspirant derivative of aluminum coated with a degraded starch selected from the group consisting of waxy cornstarch degraded by hydrolysis to a Stormer viscosity of 85 and ordinary cornstarch degraded by hydrolysis to a Stormer viscosity of 65.

13. The antiperspirant composition of claim 12 wherein said antiperspirant derivative of aluminum is basic aluminum hydrochloride.

14. The antiperspirant agent of claim 1 wherein said antiperspirant derivative of aluminum is selected from the group consisting of basic aluminum hydrochloride, chlorhydroxy aluminum lactate, complex of aluminum hydroxy chloride and propylene glycol, 2-chloro-5-ethoxy carbonyl-4-methyl-1,3,2-dioxalumin, 2-chloro-5,5-bis-(ethoxy carbonyl)-1,3,2-dioxalumane, basic aluminum bromide, 2-chloro-5-cyano-5-ethoxy carbonyl-1,3,2-dioxalumane, 2-chloro-4-ethyl-6-methyl-1,3,2-dioxalumane, 2-chloro-4-propyl-5-ethyl-1,3,2-dioxalumane, 2-chloro-5-ethoxy carbonyl-4-ethoxy-1,3,2-dioxalumin, 2-chloro- 5-acetyl-4-methyl-1,3,2-dioxalumin, bis-(N-oxypyridyl-2-thio) aluminum bromide, bis-(6-methoxy-N-oxypyridyl-2-thio) aluminum bromide and bis-(4-chloro-N-oxypyridyl-2-thio) aluminum chloride.

15. An antiperspirant agent in the form of a dry powder comprising microcrystals of an antiperspirant derivative of aluminum coated with a starch degraded by acid hydrolysis which gels in water at a temperature lower than 100° C so as to provide an atomizable gel having a starch concentration between 5-30 weight percent thereof, wherein the weight ratio of antiperspirant derivative of aluminum to starch (dry basis) is between 1:10 and 1:1, and wherein said antiperspirant derivative of aluminum is selected from the group consisting of basic aluminum hydrochloride, basic aluminum hydrobromide, complexes of aluminum hydroxy chloride with propylene glycol, aluminum phenosulfonate, chlorohydroxy aluminum allantionate, dihydroxy aluminum allantionate, complexes of chlorohydroxy aluminum with propylene glycol, chlorohydroxy aluminum lactate, aluminum sulfamate, 2-chlorodioxalumane derivatives, dioxalumane or dioxalumin derivatives substituted by electro-attractive groups, aluminum derivatives of pyridine, and their mixtures.

16. An antiperspirant composition comprising in a cosmetic vehicle suitable for topical application to human skin and antiperspirant agent of claim 15 in an amount of 2-10 percent by weight of said composition.

17. An antiperspirant agent in the form of a dry powder comprising microcrystals of basic aluminum hydrochloride coated with a starch degraded by acid hydrolysis which gels in water at a temperature lower than 100° C so as to provide an atomizable gel having a starch concentration between 5-30 weight thereof, wherein the weight ratio of antiperspirant derivative of aluminum to starch (dry basis) is between 1:10 and 1:1.

18. An antiperspirant composition comprising in a cosmetic vehicle suitable for topical application to human skin the antiperspirant agent of claim 17 in an amount of 2-10 percent by weight of said composition.

19. A process for preparing the antiperspirant agent of claim 1 in the form of a dry powder comprising introducing an aqueous gel of said degraded starch containing in solution an antiperspirant derivative of aluminum into an atomizer dryer, the temperature of air at the inlet of said dryer ranging from 200°–230° C and the temperature of the air at the outlet of said dryer being between 110°–120° C, said aqueous gel having a starch concentration between 5–30 percent by weight and the weight ratio of antiperspirant derivative of aluminum to starch (dry basis) being between 1:10 and 1:1.

20. The process of claim 19 wherein said aqueous gel is obtained by producing a suspension of said starch in cold water, heating said suspension to a temperature of 80°–90° C so as to impart fluidity thereto and adding an antiperspirant derivative of aluminum in crystalline form or in the form of an aqueous solution thereof.

21. The process of claim 20 wherein the concentration of degraded starch in the aqueous gel is between 10–15 weight percent thereof.

* * * * *